United States Patent [19]

Vaillancourt

[11] Patent Number: 4,610,683
[45] Date of Patent: Sep. 9, 1986

[54] SUCTION NEEDLE

[75] Inventor: Vincent L. Vaillancourt, Livingston, N.J.

[73] Assignee: MANRESA, Inc., Hillsdale, N.J.

[21] Appl. No.: 755,838

[22] Filed: Jul. 17, 1985

[51] Int. Cl.4 ............................................. A61B 19/00
[52] U.S. Cl. ................................. 604/405; 604/411; 604/45
[58] Field of Search ......................... 29/516, 517, 520; 604/44–45, 164–168, 405, 411, 414, 900; 141/329–330; 222/81

[56] References Cited

U.S. PATENT DOCUMENTS

| | | | |
|---|---|---|---|
| 2,168,270 | 8/1939 | Paisley et al. | 604/405 |
| 2,473,153 | 6/1949 | Lager | 604/252 |
| 2,541,272 | 2/1951 | Murphy | 604/44 |
| 3,332,272 | 7/1967 | Tonchen | 29/516 |
| 3,599,637 | 8/1971 | Schwartz | 604/167 |
| 3,608,550 | 9/1971 | Stawaki | 604/414 |
| 3,662,752 | 5/1972 | Yokoyama | 604/405 |
| 3,739,778 | 6/1973 | Monstere, Jr. et al. | 604/167 |
| 3,851,647 | 12/1974 | Monestere, Jr. et al. | 604/167 |
| 3,915,168 | 10/1975 | Monestere, Jr. et al. | 604/164 |
| 3,916,504 | 11/1975 | Thorne et al. | 29/516 |
| 3,938,520 | 2/1976 | Scislowicz et al. | 604/414 |
| 4,096,860 | 6/1978 | McLaughlin | 604/44 |
| 4,270,535 | 6/1981 | Bogue et al. | 604/164 |
| 4,286,372 | 9/1981 | Batcheller | 29/516 |
| 4,537,593 | 8/1985 | Alchas | 604/411 |
| 4,543,101 | 9/1985 | Crouch | 604/411 |

*Primary Examiner*—C. Fred Rosenbaum
*Assistant Examiner*—Michelle N. Lester
*Attorney, Agent, or Firm*—Ralph R. Roberts

[57] ABSTRACT

This suction needle device is used to transfer liquids such as cytotoxic drugs from a stoppered container to a syringe. This device has a sharpened needle which is conventionally attached to a hub. A housing is adapted and is mounted on the shank of this needle and a tubular sleeve is disposed in a telescope fashion around this shank and one end of the sleeve is secured in this housing. The stopper is disposed to be entered by the sharpened needle and sleeve and provides a seal when so penetrated. A crimping tool provides opposed and longitudinally displaced localized crimps to deform the sleeve to the extent that a positive engagement with the shank of the needle is made. The crimps are limited enough to provide positive securing of the sleeve without bending or otherwise affecting the interior capacity of the needle. The shank of the needle is sealed against exterior air reaching the conduit between the outer diameter of the needle and inner diameter of the sleeve. A hydrophobic filter is mounted in one end of the housing to filter the air within or as it enters the container.

20 Claims, 14 Drawing Figures

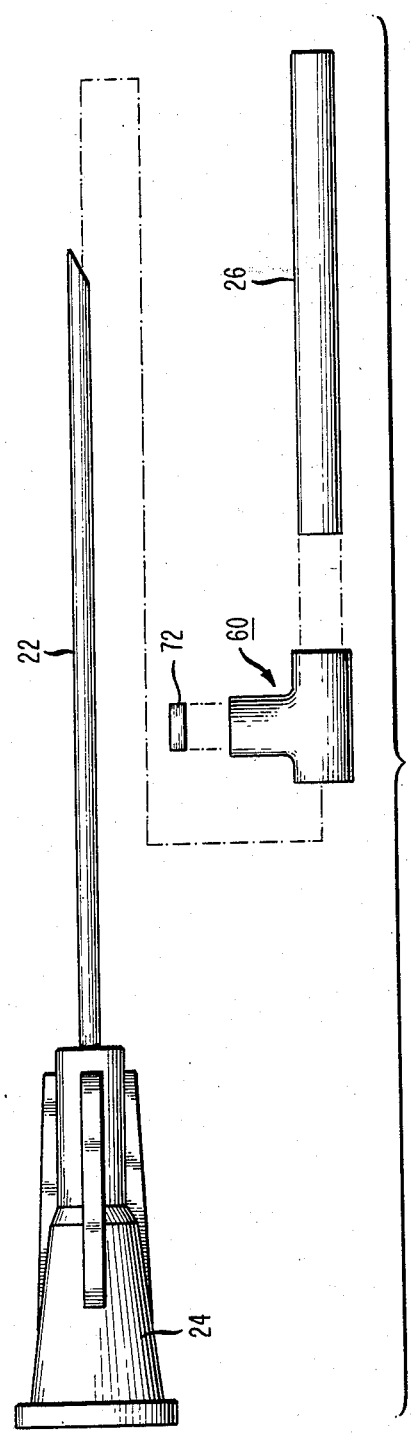
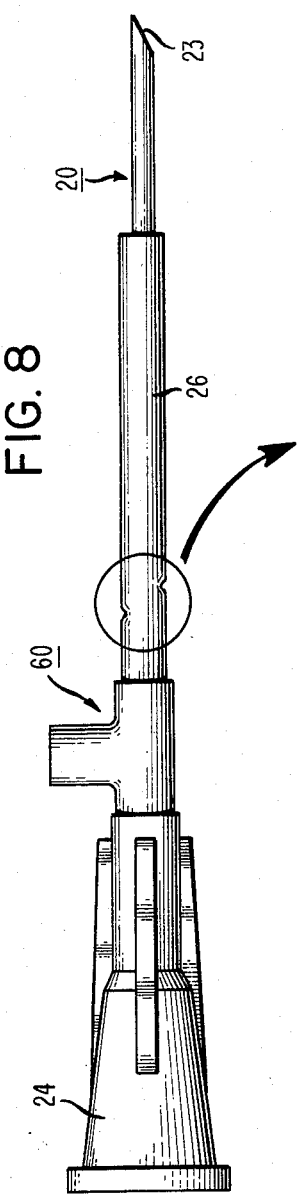
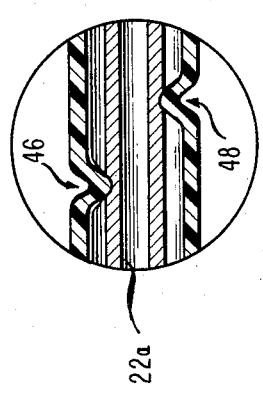
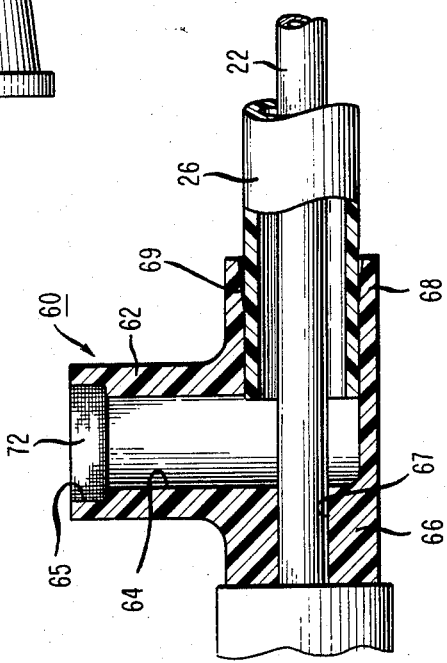
FIG. 7
FIG. 8
FIG. 10
FIG. 9

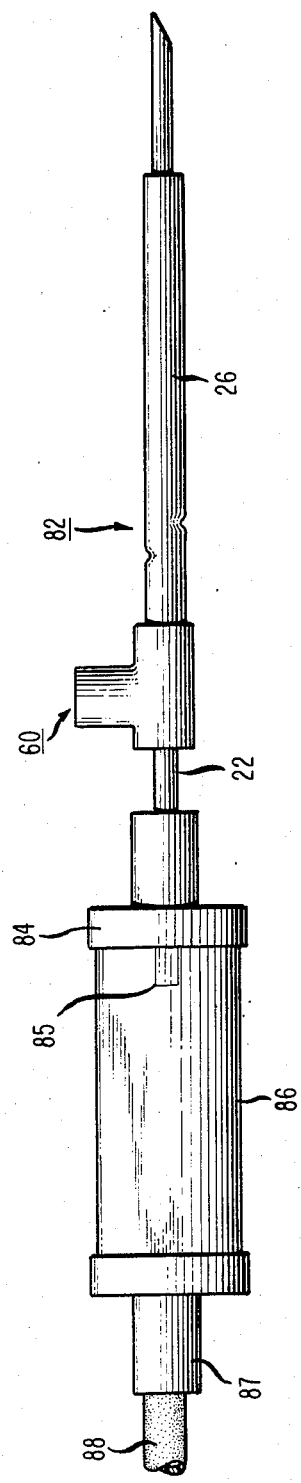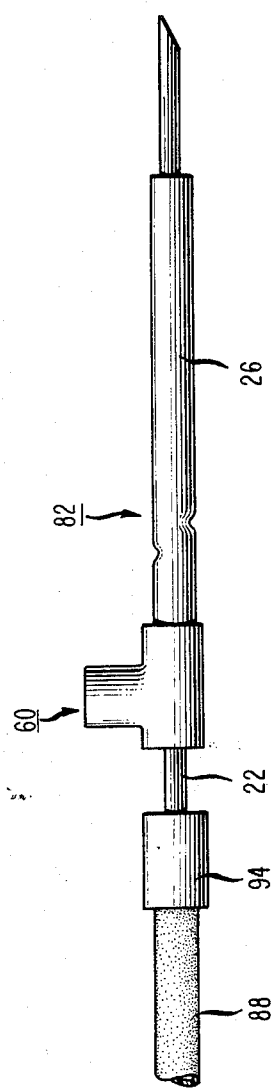

ized during the procedure. As a result, a condition

4,610,683

SUCTION NEEDLE

CROSS-REFERENCE TO RELATED APPLICATIONS

This application provides apparatus or a device that provides venting or an air passageway from and to the interior of a vial. Applications directed toward similar subject matter include application Ser. No. 509,236, as filed June 29, 1983, and entitled "Vent Needle Assembly." Another application is Ser. No. 567,877, as filed Jan. 3, 1984, and entitled "Needle with Vent Filter Assembly." The referenced applications are filed in the name of the applicant of this invention.

BACKGROUND OF THE INVENTION

1. Field of the Invention

The present invention relates to hypodermic needles used for injecting drugs into parenteral vials and/or removing the contents after mixing. Air venting of these vials is provided with this apparatus. Needles used with syringes are found in the general class of "Surgery." Withdrawal of the fluid contents from vials creates negative pressure problems and this invention is directed to providing venting of a vial.

Venting of the stoppered vial is desirable and necessary because of the noted negative pressures developed as and while the fluid is withdrawn from the vial. Constant and continued venting of the vial eliminates this problem of negative pressure. Drawbacks are present in commonly-used and -known procedures. In a procedure using two needle punctures, every time a vial is punctured there is a risk of contamination; it is evident that the fewer times a container needs to be punctured, the more aseptic the interior. It is also to be noted that this procedure is a very clumsy procedure as the vial must be held while securing two needles and syringe which are attached thereto. This procedure requires much manipulation.

2. Description of the Prior Art

Heretofore, small volume parenteral fluid containers have been pierced with hypodermic needles connected to syringes to inject fluid for reconstitution. After reconstitution the parenteral vial is repunctured and the contents removed. Alternately, a hypodermic needle-syringe combination is left within the vial while it is shaken and then the mixed drug is removed. Unfortunately, in this system the parenteral vial becomes pressurized during the procedure. As a result, a condition can and does occur, which is known as "blowback," in which particles of drug are blown into the air. This "blowback" can be very harmful to the personnel preparing such drugs. These hazards are well documented. To overcome these hazards, it is recommended that the reconstituting vial be vented at all times.

A careful pre-Ex search was made in the known art and in art which might indicate the construction of the suction needle apparatus of this invention. Swaging of two tubular members is very common and well known. Swaging is usually used for joining or connecting like size tubing extents. For the purpose of effecting such joining, an end is expanded sufficiently to provide nesting. Patents showing this procedure are U.S. Pat. No. 1,703,037 to Heck, as issued Feb. 19, 1929, and U.S. Pat. No. 4,114,930 to Perkins et al., as issued Sept. 19, 1978. In addition to the above cross-referenced applications of the present inventor, attention is directed to U.S. Pat. No. 3,903,887 to Antoshkiw, as issued Sept. 9, 1974. Also of note is U.S. Pat. No. 3,527,025 to Kinne, as issued Sept. 8, 1970, which shows using indenting apparatus which, as shown, bends the interior wire. An intending tool is shown in U.S. Pat. No. 3,332,272 to Tonchen, as issued July 25, 1967. As shown, a conduit and coupling are secured by the indenting tool. A very recently issued U.S. Pat. No. 4,505,709, as issued to Froning et al., on Mar. 19, 1985, is also noted, but this device requires two needles arrayed side by side and a special hub device which carries the needles as separate members and still requires the syringe to have an additional conduit. The present invention is much less elaborate. Also of note in U.S. Pat. No. 3,599,637 to Schwartz, as issued Aug. 17, 1971, and shows the use of flexible tubing with a penetrating needle. This needle is designed to be removable from the flexible tubing. As far as is known, it is novel to provide the concept of a suction needle using a stainless steel needle conventionally secured to a syringe hub while providing and using a second and larger sleeve cannula as a vent conduit and securing this second sleeve or cannula with crimping means so that the sleeve tightly engages the first needle while not altering the function or size of the first needle and vent conduit.

SUMMARY OF THE INVENTION

This invention may be summarized, at least in part, with reference to its objects.

It is an object of this invention to provide, and it does provide, a needle assembly in which an air venting means is provided by and with an outer sleeve. The sharpened needle provides initial penetration of a vial stopper and is in a very close proximity to the sleeve carried by and on a syringe and provides an air vent adapted to prevent unwanted "blowback" and developed vial pressures.

It is a further object of this invention to provide, and it does provide, a penetration needle adapted to provide an air vent passageway and having a hub portion that has an air vent and filter. This penetration needle is of stainless steel and secured to a hub or molded member of plastic, with the socket sized and adapted to be mounted on the discharge end of a syringe. This assembly may also be used as a replacement spike so as to supply air to an administration set. This needle assembly, when used with a syringe for injection and with the outer sheath portion is crimped in at least two places and is not removable and is discarded before the drug is to be injected into a patient. The crimps as shown and described hereinafter are at least two in number and provide a positive non-slip lock of an outer sleeve to the lumen of a needle without distortion of the lumen.

The device includes a standard hypodermic (injection) needle attached to a female luer hub capable of being attached to a luer nose of a conventional syringe. A second cannula or sheath member is also of stainless steel tubing and is just a little larger than the needle. The interior spacing between the outer diameter of the needle and the interior diameter of the cannula or sheath is preferably about two- to six-thousandths of an inch total. This nested-array spacing is an example of a reduced-to-practice device for a twenty-gauge needle.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there have been chosen two specific embodiments of the suction needle as adopted for use with a vial having a resilient stopper and showing a preferred means for constructing and assembling this suction needle assembly. These specific embodiments have been chosen for the purposes of illustration and description as shown in the accompanying drawings wherein:

BRIEF DESCRIPTION OF THE DRAWINGS

FIG. 7 represents a side view in a diagrammatically expanded condition and illustrating the relationship of the several components providing this alternate suction needle assembly;

FIG. 8 represents the diagrammatic side view as in FIG. 1, but with the T-shaped connector housing of FIG. 6 in mounted condition rather than the elbow member of FIG. 1;

FIG. 9 represents a partly fragmentary side view similar to that of FIG. 2, but with the T-shaped connector housing of FIG. 6;

FIG. 10 represents the enlarged side sectional view essentially as in FIG. 3 and showing the crimping of the outer sleeve to the shank of a needle;

FIG. 11 represents a side view of a suction needle assembly, much as in FIG. 8, but with the secured end of the needle retained by a molding also adapted to hold and retain one end of the flexible tubular portion of a drip chamber and with the other end of the drip chamber having an end closure and a tubing connection;

FIG. 13 represents a side view of a suction needle assembly, like that in FIG. 11, but with the secured end of the needle retained by a molding adapted to receive and retain a length of flexible tubing.

EMBODIMENT OF FIG. 1 THROUGH FIG. 4

Figure 1:
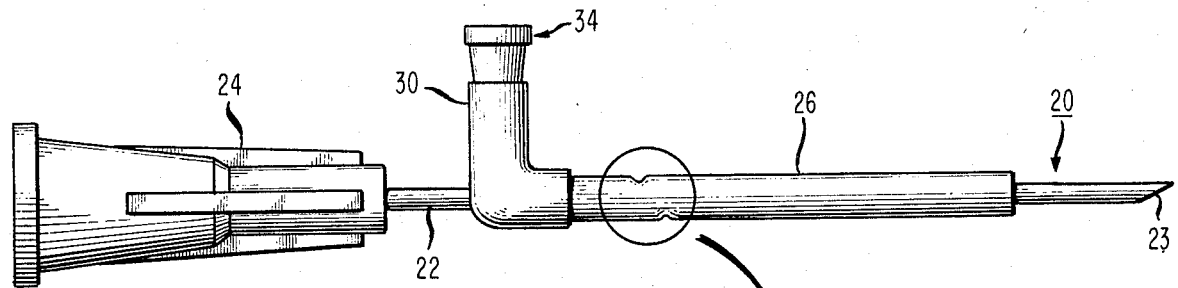
FIG. 1 represents a side view, partly diagrammatic, in an enlarged scale and showing a suction needle in one embodiment.

Referring next to the drawings and the suction needle illustrated therein, there is shown in enlarged scale a suction needle device designed to provide a flow of filtered air to a stoppered vial or container. During withdrawl of the contents of the fluid in the vial or container by a syringe, air is required to prevent the interior of the vial from developing an excessive negative pressure. In FIG. 1 a conventional sharpened needle, generally identified as 20, is shown with a shaft portion 22 having a shaprened end 23. This needle is secured to a molded hub 24 which is also very conventional. To provide an air-conducting path, a stainless steel tubing portion or sleeve 26 is provided and it is contemplated that this sleeve portion be a blunt tip at one end and cut off square at the other end. The distal end of this sleeve toward the sharpened end of the needle is open and as the sleeve portion is larger on its inner diameter than the outer diameter of the needle shank, an air passageway is provided.

Figure 4:
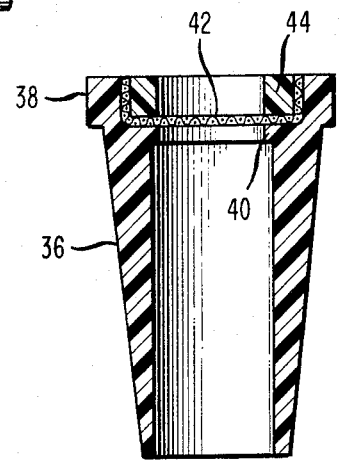
FIG. 4 represents a side sectional view in an enlarged view from that of FIG. 1 and showing the configuration of a filter cup secured in one end of the plastic elbow.

The other end of sleeve member 26 is mounted in an elbow member 30 which may be a length of bent rubber tubing or may be of molded PVC. Whether of rubber or of PVC or like plastics, it is contemplated that the shank of the needle may pass through the left curved wall portion at 32 and provide a seal excluding the passing of air or gas. A filter cup, generally identified as 34, is formed separately. As seen, this cup has a taper and is mounted in the resilient upper end of elbow member 30 to provide a secured and air-tight mounting. As shown by the arrows, air may flow into and from the end of the sleeve member 26. In FIG. 4, the cup 34 is shown in a sectional view. The tapered body 36 is a molded member, usually of plastic, and rigid or semi-rigid enough that the walls are not distorted by an inward force developed by the resiliency of elbow member 30. At the distal or upper enlarged end 38 of this cup 34 is formed a stop shoulder 40 which provides a shelf on which a filter disc 42 is seated. A ring-like retaining member 44 is inserted into the interior open top of cup 34 and without solvent means secures this filter in place. Solvent or other cement may be used if desired. The ring-like retaining member 44 may have a spoke to reinforce this ring but, with or without a reinforcement, the filter 42 is retained while passing air or gas. It is contemplated that the filter 42 be hydrophobic.

Figure 3:
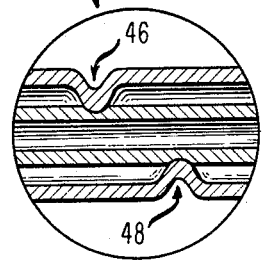
FIG. 3 represents a side sectional view in a greatly enlarged scale and depicting a crimp securing of the outer sleeve to the shank of the needle.

After or before the elbow 30 is secured and/or mounted on and to the tubular sleeve 26, this sleeve is longitudinally secured to the shank 22 of the needle by crimping with a tool to form crimps 46 and 48. As shown in FIG. 3, the two crimps lock the sleeve in place on the lumen of the needle. These crimps may be on the same side or offset as shown. These crimps, although limited in their engagement, prevent slip along the needle shaft and although a sure lock is effected these crimps are not sufficient to appreciably change the lumen of the needle. For this reason, the crimping tool or apparatus has a limiting stop to prevent appreciable distortion of the needle lumen. More than two crimps may be utilized but are not needed, but only one crimp allows for play between the sleeve and shank of the needle. The two crimps do not appreciably diminish the capability of air to flow interior of the sleeve. An increase in crimps reduces the air flow capability.

ALTERNATE EMBODIMENT OF FIG. 5

Figure 5:
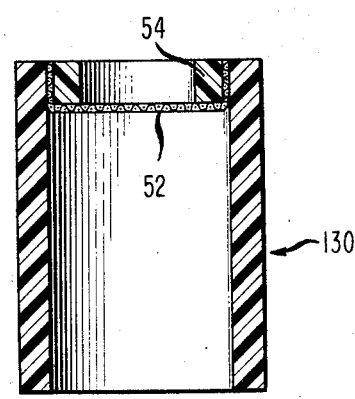
FIG. 5 represents a side sectional view of an alternate securing of a filter means into the plastic elbow of FIG. 2.

In FIG. 5, the elbow 130 is shown with an upper distal end 50 having a cup-shaped filter 52 inserted therein. A ring 54 is used to retain this filter 52 in position. The sealing is contemplated to be by solvent or the like. This embodiment contemplates the elbow housing 130 be made of a flexible plastic such as PVC, but rubber may be used.

EMBODIMENT OF FIGS. 6, 7, 8, 9 AND 10

Figure 2:
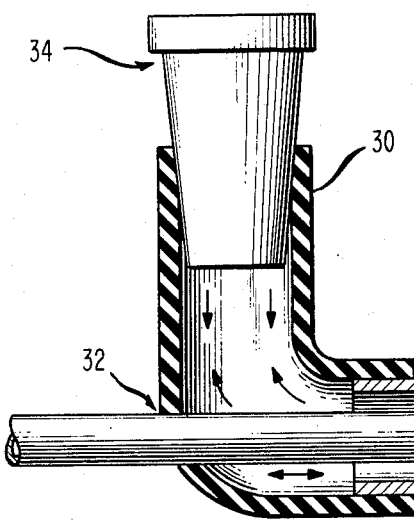
FIG. 2 represents a partially fragmentary and partly sectional side view in an enlarged scale from that of FIG. 1 and showing the positioning and passing of a needle shank through a rubber or plastic elbow member into an outer sleeve.
Figure 6:
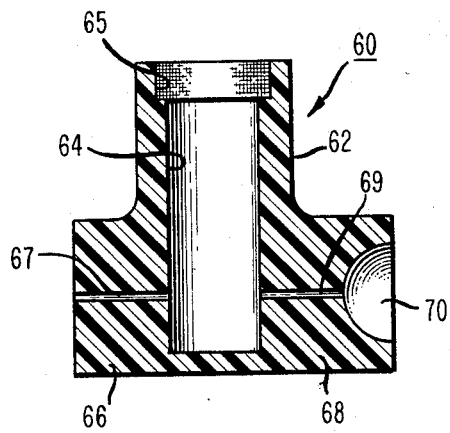
FIG. 6 represents a side sectional view of an alternate filter connector device in which a more-or-less T-shaped connector housing has means for passing and securing a needle while the opposite end is adapted to receive and retain a metal sleeve, with the stem portion of the connector housing adapted to receive and retain a filter member.

Referring next to the suction needle assembly as shown in FIGS. 6, 7, 8, 9 and 10, it is also contemplated that, rather than an elbow member 30 as is shown in FIG. 2, there is an alternate construction to receive and retain the tubular outer sleeve 26. As seen in FIG. 6, a molding, generally identified as 60, is molded in generally a T-shape. This molding has a stem portion 62 in which a stepped recess 64 and 65 is formed, with this larger recess being identified as 65. A left portion 66 of the molding is shown as formed with a small through aperture 67 or have a guideway formed for the passage of the shank 22 of the needle. Whether an aperture is provided or the needle is forced through the left wall of the molding 60, the shank 22 of the needle passes through this resilient wall 66 and a gas- or air-tight seal is formed around this shank. The opposite or right end of this molding is identified as 68 and not only has an aperture 69, but an enlarged recess 70 that is adapted to receive and retain the end of sleeve 26. As depicted, the sleeve 26 is advanced to be fully seated and retained by the right end 68 of the molding 60. The penetration of the sleeve 26 into this end of the molding is only sufficient to provide an air seal between 26 and 60 and provide a passageway to 64. In no case should or can the sleeve be inserted to the extent as to prevent a flow of gas or air from the end of the sleeve to and through conduit 64 to and through filter 72.

A filter 72 is mounted in the counterbore 65 and may be a pressed fit or may be secured by a solvent seal and, if desired, may also have a retaining ring 44 as in FIG. 4 above. In assembly it is desired that the left portion 66 of the molding 60 be brought into the desired position, usually next to the hub 24. This will locate the opening 64 for the forcing of sleeve 26 into recess 70 and through 68 to the opening 64.

In FIG. 7, the diagrammatic representation of assembly of the suction needle device shown particularly in FIG. 8 shows the arrangement of components as and when automatic assembly is to be made. The needle shank 22 is mounted in hub 24 and the sharpened end 23 is urged or pushed through the left wall 66 of the molding. If a small aperture 67 is provided, this can be used as a guideway. This needle exits through the right end or wall 68 and an aperture 69 therein (see FIG. 6). The enlarged recess 70 provides a piloting and seating means for the sleeve 26 which is sealed in aperture 69. The filter 72 is mounted before the assembly of the components.

The assembly, as depicted in FIG. 9, shows shank 22 of the needle passing through the left wall 66 of the molding 60 and then said shank continues rightward through sleeve 26 to the sharpened end (FIG. 8). The sleeve 26, after positioning in the molded T-shaped member 60, is secured by crimping as in FIG. 10. The crimping is very similar to or is identical to the securing described in connection with FIG. 3 above.

The devices of FIGS. 1 and 8 are contemplated to be very low in cost and provide a one-time use. Inexpensive cost is desired so as to reduce the expenses particularly incurred in and with treatments using potent drugs. This device, whether the embodiment of FIG. 1 or the embodiment of FIG. 8, is contemplated to provide filtered venting of a vial. The crimping of the sleeve 26 to the shank 22 provides only very localized indenting and limited deformation so as not to impair the needle lumen's fluid flow characteristics while providing a secure lock of the sleeve to the needle. The needle point 23 penetrates the resilient stopper of the vial followed by the sleeve 26. Because of potential coring of the stopper vial, needle sizes for this suction needle device are a maximum of eighteen gauge. The sleeve is conventionally of stainless steel with a wall thickness of four-to ten-thousandths of an inch. This arrangement allows for air passage in the annular space which is sufficient for venting the vial. The use of this suction needle is usually with antineoplastic drugs with which the attendent should not come in contact.

The crimps 46 and 48 are contemplated to be tapered or knife-like indents. Crimp securing, as shown in Kinne, U.S. Pat. No. 3,527,025, wherein the wire is bent from a straight line, is not anticipated or desired. The crimp is very localized and deforms the sleeve 26 and, as shown, the crimp engages the outer surface of the needle only sufficiently to tightly engage the needle shank. For this reason, the apparatus for producing the crimp is regulated by a stop means so as to limit the deformation of the sleeve 26 and engagement of the shank 22. The crimps are anticipated to be only two in number and staggered as shown in FIGS. 3 and 10. This does not preclude more crimps and does not preclude a plurality of crimps along or substantially along the same side.

The filter means is anticipated to exclude unwanted air-carried bacteria and, if any fluid from the vial contents accidentally is brought to the filter, this filter provides a fluid barrier. Whether the filter membrane is as in FIGS. 4, 5 or 9, it is anticipated that the filter membrane will be sufficiently supported so as not to tear in use or be distorted from its intended use. The shank 22 of the needle is sealed to the elbow member 30 or T-shaped member 60 and, with the sleeve 26, provides a device that is sealed to the surrounding atmosphere. Solvent or cement to provide this seal may be provided if needed.

EMBODIMENTS OF FIGS. 11 THROUGH 14

Referring next, and finally, to the suction needle as exemplified in FIGS. 11 through 14, this device is shown as used with intravenous feeding. A supply bottle 75 contains the desired fluid identified as 76. A resilient stopper or cap 78 closes the end of this bottle or container. A hanger 79 is disposed to provide suspension means for this container to a customarily-provided hook 80. The vent needle device, shown assembled in FIG. 8 but absent hub 24, is utilized and as an assembly is generally identified as 82.

Figure 12:
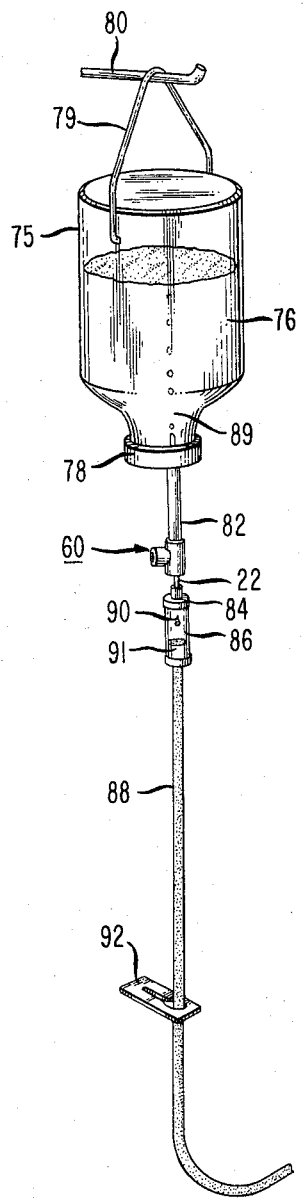
FIG. 12 represents an isometric view, partly diagrammatic, and showing the suction needle assembly and drip chamber in inserted position and condition to remove fluid from an intravenous container.

In FIGS. 11 and 12, the shank 22 of the needle extending to the left of molding 60 is depicted as mounted in a molded retainer 84 having a drip extension member 85 therein and adapted to provide a fluid path from the bore of the needle into this drip chamber. The drip chamber also includes the flexible tubular portion 86 terminating with and attached to an end cap 87 to which is connected a flexible tubular conductor 88. As seen in FIG. 12, air 89 flows into the bottle to replace liquid which flows usually in drops 90 into the drip chamber. A fluid level 91 is usually maintained at the bottom of this drip chamber. A clamp 92 is depicted to close off the flow of fluid to the patient. Any clamp means if desired may be used.

Figure 14:
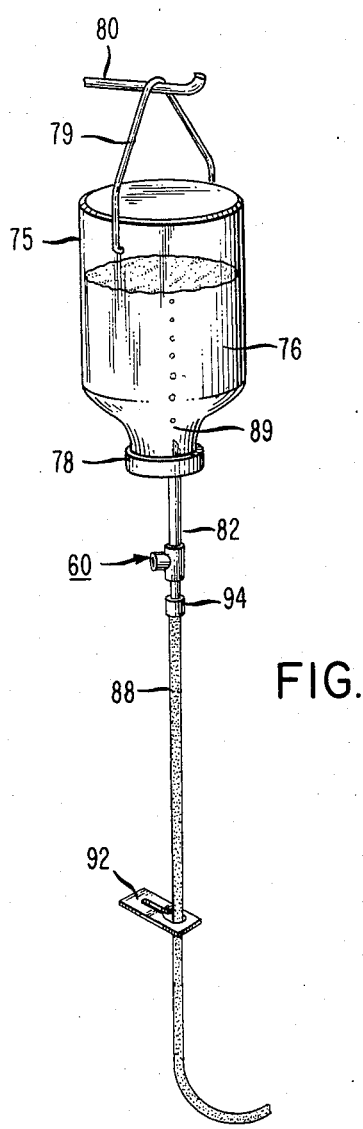
FIG. 14 represents a side view of a suction needle assembly, like that of FIG. 13, in inserted position and condition to remove fluid from an intravenous container.

In FIGS. 13 and 14, the suction needle is also shown as used with a bottle or container 75 with fluid contents 76, but rather than a drip chamber this suction needle has the shank 22 secured to a molded retainer 94 and to this is secured the flexible tubing 88 identified above. This embodiment may be used to fill infusion bottles in the hospital pharmacy.

It is to be noted that the embodiments of FIGS. 12 and 14 depict rigid containers, but other containers may also be emptied using this suction needle, among which are flexible pouches. The fluid containers are not a part of this invention and neither are tubing, shut-off valves and drip chambers as they are conventional and well known. What is believed to be novel is the inexpensive suction needle of this invention and the discovery that the tubular sleeve may be secured to the shaft of the needle by simply making two or more crimps without appreciably distorting the lumen as to flow capacity.

The needle used with this device is used for removing drugs from a container. This needle is not contemplated to be used with a patient and the skin of this patient is not to be penetrated with this needle because of the attached sleeve. This sleeve is shown in FIG. 2 as tubular metal (stainless steel), but may be a plastic (FIG. 9) if and when such plastic is permanently deformable and having the characteristics of metal. The needle shank 22 is preferably sharpened at 23 to decrease the effort or force needed to pass through the housing or the stopper to be penetrated. The sleeve 26 is usually of a thin wall to reduce the effort of passing through the stopper. The sleeve is conventionally cut off substantially normal to its axis with one end beveled, but other cutoff configurations may be provided including a squared edge. For economical reasons, the housings 30 or 60 are preferably molded of a partially resilient material such as PVC, plastic or rubber, but this is not to preclude molding the housing of other materials and using a cement to provide an air-and-fluid seal around the shank 22 of the needle.

It is to be noted that in FIGS. 13 and 14, the needle 22 is depicted as attached to a tubular molding 94 but, if desired, this member 94 may not be required and thus eliminated and the left or downwardly disposed end of said needle may be attached directly to a flexible conductor 88. In either condition the sleeve 26 is secured by two or more crimps to assure during use fixed securing of said sleeve to the needle to prevent any and all movement of the sleeve 26 on the along the needle.

Terms such as "left," "right," "up," "down," "bottom," "top," "front," "back," "in," "out" and the like are applicable to the embodiments shown and described in conjunction with the drawings. These terms are merely for the purposes of description and do not necessarily apply to the position in which the suction needle and sleeve may be constructed or used.

While particular embodiments of the suction needle device have been shown and described, it is to be understood that the invention is not limited thereto and protection is sought to the broadest extent the prior art allows.

What is claimed is:

1. A suction needle device for fluid withdrawl and venting the interior of a stoppered vial or container, said device including:
   (a) a hollow metal needle having a shank and a hub;
   (b) a housing having first and second open ends and a wall portion therebetween, said housing being adapted to receive said shank through said wall portion and to provide a sealed connection between said shank and said wall portion, said housing being disposed so that a shank so received will extend from said wall portion through said second end;
   (c) a thin-walled tubular sleeve mounted in and secured to said second housing end so as to extend outwardly therefrom, said sleeve having a length less than that of said shank and having an internal diameter larger than the outer diameter of said shank, said sleeve being coaxially aligned with the portion of the shank that extends through the second housing end so as to provide a substantially annular space therebetween;
   (d) an air passageway within the housing and in flow communication with the annular space and the first housing end, the first end of the housing being provided with means for filtering air that passes between the air passageway and the atmosphere; and
   (e) at least two localized crimps formed in said tubular sleeve, the crimps being longitudinally displaced and being only sufficient to locally deform the sleeve without substantially deforming the lumen of the shank disposed therethrough.

2. A suction needle device, as in claim 1, wherein the stopper of the vial is formed from resilient material and the entering end of said needle is sharpened so as to be able to pierce the stopper.

3. A suction needle device, as in claim 2, wherein the housing comprises a tube of resilient material that is bent into a elbow shape, the resiliency of the tube wall providing the sealed connection between the shank and the wall portion.

4. A suction needle device, as in claim 3, wherein the filter is secured in a molded cup member, the cup member being tightly secured in the first end of the housing.

5. A suction needle device, as in claim 1, wherein the crimps are V-shaped and the longitudinal displacement and depth of penetration is established by mechanical means.

6. A suction needle device, as in claim 1, wherein at least one of said at least two crimps is disposed on the opposite side of the sleeve from the other of said at least two crimps.

7. A suction needle device, as in claim 1, wherein the housing is T-shaped, said first open end being provided on the stem portion of the housing, and said wall portion and said second open end being provided, respectively, at the opposite ends of the cross bar of the housing.

8. A suction needle device, as in claim 7, wherein the housing is formed from plastic, the needle and sleeve being secured in an air- and fluid-tight manner by solvent or cement.

9. A suction needle device, as in claim 7, wherein the housing is formed from flexible plastic, the needle and sleeve being secured in an air-and fluid-tight manner by the resiliency of the plastic.

10. A suction needle device, as in claim 2, wherein the hub of the needle is coupled to a drip chamber and both the sharpened end of the needle and the end of the thin-walled tubular sleeve are adapted to enter the resilient stopper.

11. A suction needle device, as in claim 2, wherein the hub of the needle includes a connector means for flexible tubing and both the sharpened end of the needle and the end of the thin-walled tubular sleeve are adapted to enter the resilient stopper.

12. A suction needle device for fluid withdrawl and venting the interior of a stoppered vial or container, said device including:
  (a) a hollow needle having a distal shank portion;
  (b) a housing having first and second open ends and a wall protion therebetween, said housing being adapted to receive said shank portion and to provide a connection between said shank and said wall portion, said housing being disposed so that a shank portion so received will extend from said wall portion through said second end;
  (c) a thin-walled tubular sleeve mounted in and secured to said second housing end so as to extend outwardly therefrom, said sleeve having a length less than that of said shank portion and having an internal diameter larger than the outer diameter of said shank portion, said sleeve being coaxially aligned with the portion of the shank that extends through the second housing end so as to provide a substantially annular spacer therebetween;
  (d) an air passageway within the housing and in flow communiction with the annular space and the first housing end, the first end of the housing being provided with means for filtering air that passes between the air passageway and the atmosphere; and
  (e) at least two localized crimps formed in said tubular sleeve, the crimps being longitudinally displaced and being only sufficient to locally deform the sleeve without substantially deforming the lumen of the shank portion disposed therethrough.

13. A suction needle as in claim 12 wherein the needle is sharpened at one end and is secured to a molded member at the other end, the molded member having a tubing receiving and retaining means and providing flow communication between tubing coupled thereto and the needle lumen.

14. A suction needle as in claim 12 wherein the needle is sharpened at one end and is secured to a flexible tube at the other end.

15. A suction needle as in claim 12 wherein the needle is sharpened at one end and is secured to a drip chamber at the other end, the suction needle device being adapted to puncture a resilient stopper in a supply container so as to enable fluid to be delivered to the drip chamber while simultaneously venting the supply container.

16. A suction needle as in claim 12 wherein the housing comprises as a tube of resilient material that is bent into an elbow shape, the resiliency of the tube wall providing the sealed connection between the shank portion of the needle and the wall portion.

17. A suction needle as in claim 12 wherein the housing is T-shaped, said first open end being provided on the stem portion of the housing, said wall portion and said second open end being provided, respectively, at the opposite ends of the cross bar of the housing.

18. A suction needle as in claim 17 wherein the housing is formed from plastic, the needle and sleeve being secured in an air-and fluid-tight manner by solvent or cement.

19. A suction needle as in claim 17 wherein the housing is formed from flexible plastic, the needle and sleeve being secured and in an air- and fluid-tight manner by the resiliency of the plastic.

20. A method of constructing a suction needle device which is adapted to pierce the stopper of a vial or container so as to vent the interior of said vial or container during fluid withdrawl therefrom and thereby maintain the interior at substantially atmospheric pressure, the method including the steps of:
  (a) providing a conventional needle having a sharpened distal end and a proximal end;
  (b) forming and providing a housing having first and second open ends and a wall portion therebetween, passing the sharpened end of said needle through said wall portion and through said second open end, and providing a sealed connection between said needle and said wall portion;
  (c) providing a thin-walled tubular sleeve having a length less than that of the needle and having an internal diameter larger than the outer diameter of the needle, coaxially positioning said sleeve over the portion of the needle that extends through said second housing end so as to provide a substantially annular space therebetween, and mounting and securing said tubular sleeve in the second housing end;
  (d) forming an providing in the housing an air passage way in flow communication with the annular space and the first housing end and securing in said first end means for filtering air that passes between the air passageway and the atmosphere; and
  (e) forming at least two localized cromps in said tubular sleeve, the crimps being longitudinally displaced and being only sufficient to locally deform the sleeve without substantially deforming the lumen of the needle disposed therethrough.

* * * * *